United States Patent [19]

Nunogaki et al.

[11] Patent Number: 4,550,417
[45] Date of Patent: Oct. 29, 1985

[54] APPARATUS FOR COUNTING NUMBERS OF FINE PARTICLES

[75] Inventors: Yoshiaki Nunogaki; Tetsuya Kobayashi, both of Kyoto; Yasutaka Kosuge, Osaka, all of Japan

[73] Assignee: Sanki Engineering Co., Ltd., Kyoto, Japan

[21] Appl. No.: 434,487

[22] Filed: Oct. 15, 1982

[51] Int. Cl.$^4$ ............................................. G06M 11/02
[52] U.S. Cl. ...................................................... 377/10
[58] Field of Search ............................ 377/10; 356/39

[56] References Cited

U.S. PATENT DOCUMENTS

| | | | |
|---|---|---|---|
| 2,939,633 | 6/1960 | Robinson | 377/10 |
| 3,736,432 | 5/1973 | Sweet | 377/10 |
| 3,811,036 | 5/1974 | Perry | 377/10 |
| 4,191,940 | 3/1980 | Polcyn et al. | 377/10 |

*Primary Examiner*—Stanley D. Miller
*Assistant Examiner*—K. Ohralik
*Attorney, Agent, or Firm*—Armstrong, Nikaido, Marmelstein & Kubovcik

[57] ABSTRACT

An apparatus for counting numbers of microscopic corpuscles such as blood cells, comprising an optical system, a driving mechanism, a photoelectrical convertor means and a counter means. The optical means is adapted to illuminate a sample containing the corpuscles so as to irradiate magnified images onto a charge coupled device (CCD) as the convertor means having elements lined up in a row in an X-direction perpendicular to a Y-direction in which the sample is moved by the driving mechanism whereby X-directional scanning is automatically executed by the CCD without moving the sample while Y-directional scanning is conducted with a sample holder continuously moved by said mechanism comprising a drive motor and a cooperating spring. The CCD is adapted to detect the number of corpuscle images contained in each scanning line in the X-direction and thereby to produce electric signals fed to the counter means, which comprises electronic circuits for summing up these signals in respect of Y-direction.

3 Claims, 8 Drawing Figures

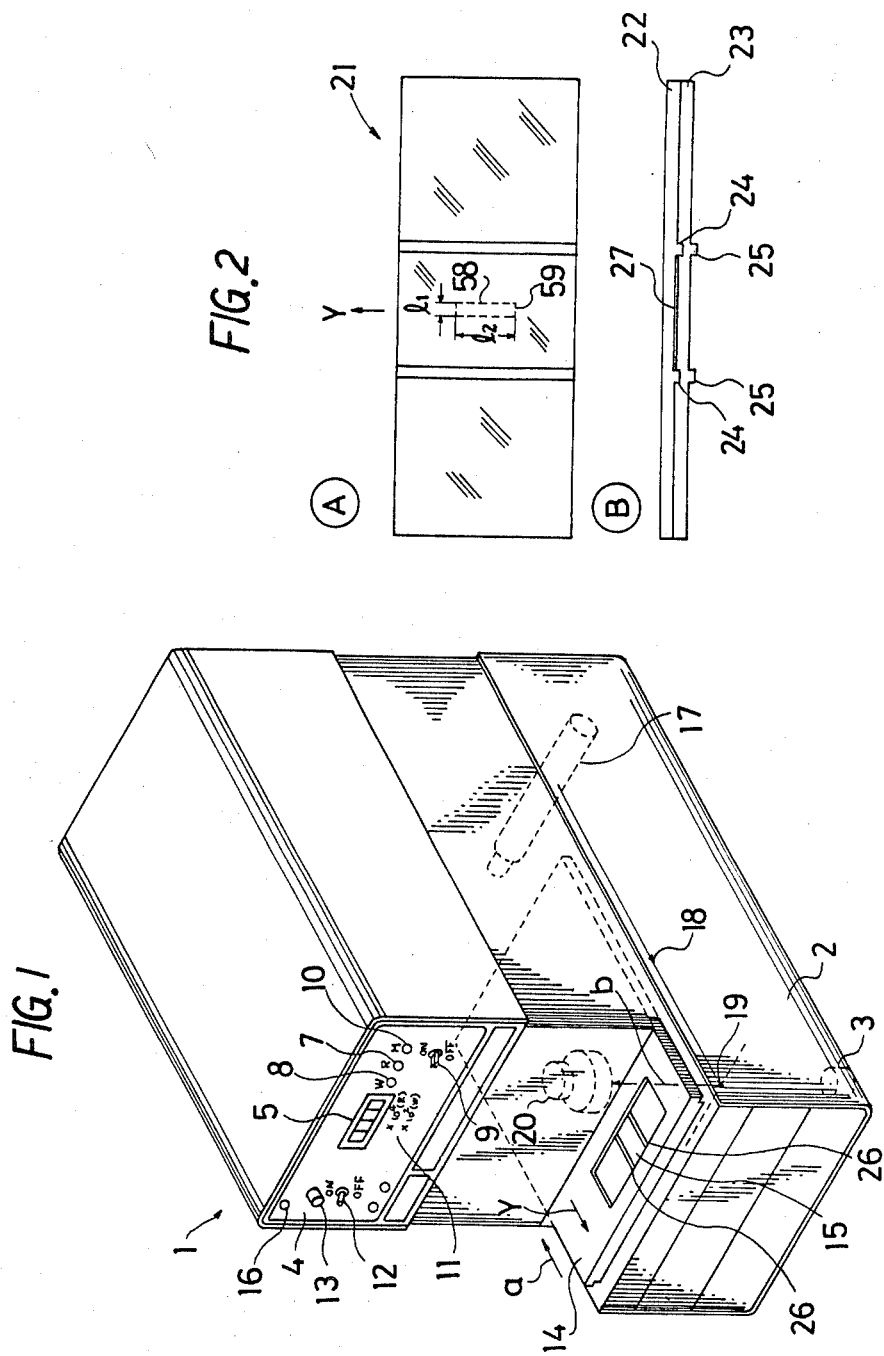

APPARATUS FOR COUNTING NUMBERS OF FINE PARTICLES

BACKGROUND OF THE INVENTION

The invention relates to an apparatus for counting numbers of microscopic fine particles such as blood corpuscles, and more particularly to an apparatus which ensures a more accurate counting of such fine particles with ease in operation.

Apparatus which have been used conventionally to this end are generally based on an impedance method or a photoelectrical scanning method. The apparatus based on the impedance method usually suffer from unfavorable disturbance caused by noises, and an opening in its detector is apt to be soon clogged with impurities or fine particles to be counted. The other known apparatus for the photoelectric scanning are highly complex in view of its mechanism for driving a sample holder and its photoelectrical or electrical mechanism, so it is difficult to operate the apparatus which unavoidably costs too much.

A more frequent blood counting is recently being required by physicians. However, blood cells in blood samples will coagulate or be broken as time passes so that correct measurements of them become difficult.

Such circumstances have given rise to a demand for a better apparatus which will enable the physicians to perform an easy rapid blood count soon after a sampling of blood. Such improved apparatus is also needed in many other fields of science and industry in which a rapid counting of fine microscopic particles must be correctly conducted.

BRIEF SUMMARY OF THE INVENTION

It is an object of the invention, therefore, to provide an apparatus suited for rapidly counting fine particles to give more correct data.

It is another object of the invention to provide an apparatus comprising an optical system for magnifying particle images, a driving mechanism for moving a sample holder, a photoelectric convertor means adapted to convert magnified optical images of the particles in the holder into electric signals, and a counting and output means arranged so as to sum up the signals into an output data.

In the invented apparatus, a sampled liquid containing fine particles to be counted is preliminarily diluted to a predetermined ratio of dilution. The sample holder is adapted to receive thereon a transparent sample plate which is suitable for retaining the diluted liquid in such a manner as to form a thin plane layer of said liquid. The optical system has a device which illuminates the plate with a parallel light stream. The optical system also is arranged such that optical images of each particle in the liquid sample may be magnified to a size large enough to respectively cover any one of a plurality sensor elements that belong to the abovesaid photoelectric convertor means. In the driving mechanism, the sample holder is adapted to move in a plane perpendicular to the optical axis of said optical system. The above mechanism has a drive device which drives the holder merely in one direction (Y-direction) which is parallel with a longitudinal side (Y-axis) of the aforementioned transparent plate while the plate is scanned in the other direction (X-direction) perpendicular to the former direction, i.e. Y-axis of said plate. The speed of the motion along the X-axis may be set high enough to sweep each scanning line across the plate in for instance 0.002 sec.

The photoelectric convertor means comprises a plurality of photoelectric convertor elements each having a fine dimension such as 15 $\mu$m square. These elements are spaced apart from each other for instance at an interval of 10 $\mu$m so as to form a line. The number of said elements is determined such that it should exceed a number of fine particles which are expected to exist on a single scanning line along the X-axis, for example the elements' number being 256. Such convertor elements receive the magnified optical images to change them into electric signals which are to be fed to a subsequent process. A kind of memory element such as a CCD (Charge Coupled Device) may be utilized as the foregoing convertor elements which are capable of "self-scanning" as described below.

The counting and output means includes a counting or control circuit and an output unit, the former being arranged so as to integrate the particle numbers detected in the X-direction by the CCD during the Y-direction scanning motion of said sample holder.

Thus the number of particles existing on the transparent plate can be now more correctly counted with an easier operation.

Other objects and advantages of the invention will become apparent in the course of following detailed description with reference to the accompanying drawings.

BRIEF DESCRIPTION OF THE DRAWINGS

FIG. 1 is a perspective view of an embodiment;

FIGS. 2A and 2B are respectively a plan view and front elevation of transparent plates in the embodied apparatus;

DETAILED DESCRIPTION OF THE INVENTION

Figure 3:
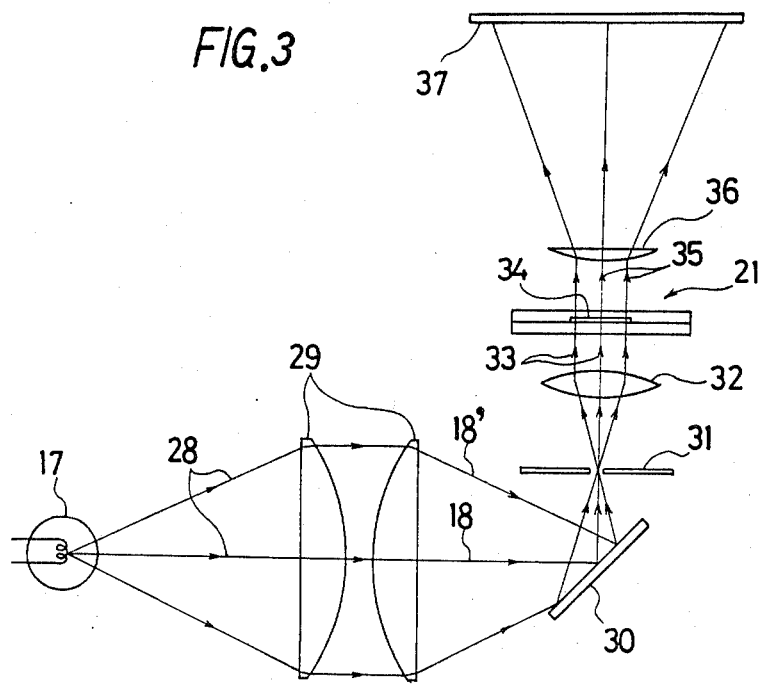
FIG. 3 is a schematic diagram of an optical system in the apparatus.

FIG. 1 illustrates an apparatus 1 in an embodiment of the invention with an optical system shown with dashed lines. The apparatus is designed for use in blood counts measurement, and the optical system is disposed within an outer casing of the apparatus. A digital counter 5 of four figures is located at the center of a panel 4, and also indicator lamps 7 and 8 are provided which are disposed near the counter so as to be utilized for switching over the apparatus from an erythrocyte count to a leucocyte count or vice versa. A power source switch 9 accompanies an indicating lamp 10. Another switch 12 and a knob 13 are for the optical system, the knob being used to adjust a light intensity of said system.

Figure 4:
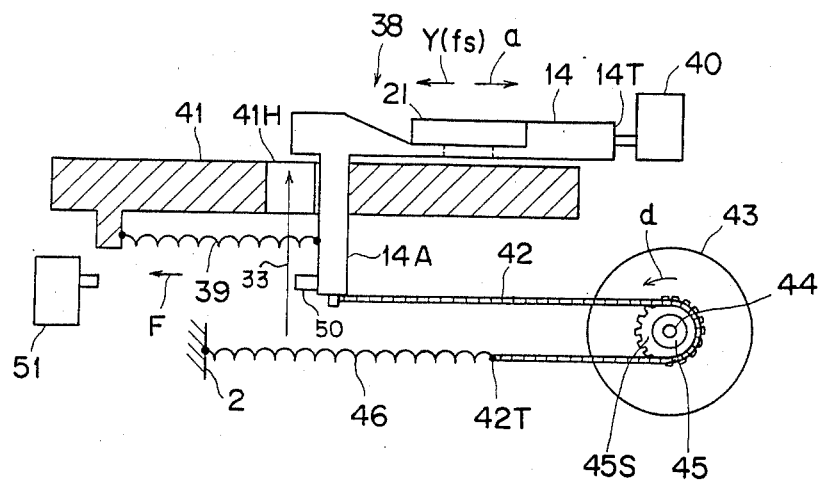
FIG. 4 is a schematic side elevation of a driving mechanism for moving a sample holder in the apparatus.
Figure 5:
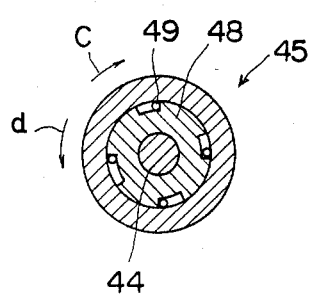
FIG. 5 is a section of a one-way clutch incorporated in said mechanism.
Figure 6:
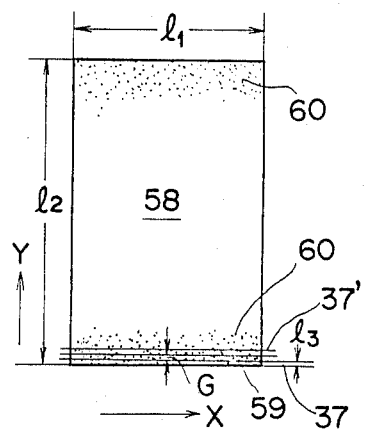
FIG. 6 shows an enlarged scanning area of the plates shown in FIGS. 2A and 2B.

A sample holder 14 has a front portion 15 to which a sample plate as shown in FIGS. 2A and 2B are mounted. The illustrated state corresponds to a condition before a measurement starts. Said plate will be set on the portion 15 by engaging it into recesses of the portion when a measurement is to be conducted, and the holder 14 will be pushed inwardly in the arrowed direction (a) until another indicator lamp 16 is switched on. The holder 14 will immediately begin to slowly move at for instance 2.2 mm/sec in the arrowed direction (Y). A driving mechanism which drives the holder in such a way is accommodated in a base 2 and has a structure as shown in FIGS. 4 to 6.

The base 2 is provided, as shown with a dashed line, with a light source 17 which emits a convergent light beam 18, the latter thereafter being reflected by a mirror positioned at 19 to advance in the arrowed direction (b) so as to irradiate the sample plate held on the holder 14 via a slit and a condenser lens. The optical system will be described hereinafter more in detail.

The numeral 20 indicates a composite sensor unit comprising an objective lens and a CCD assembly which photoelectrically converts into electric signals an optical image of a sample magnified by the objective lens to a predetermined magnifications and projection thereon.

The sample plate 21 consists of two thin transparent sheets such as glass plates 22 and 23 as shown in FIGS. 2A and 2B. Protrusions 24 of one of the glass plates 22 fit into recesses of the other plate 23, and protrusions 25 of the latter plate fit in turn into the abovesaid recesses 26 formed on the platform 15 of said sample holder 14. Said two plates 22 and 23 will define, when combined, a thin space 27 between the two protrusions 24. The space 27 may be of, for instance, 0.1 mm thickness which is sufficient to prevent the superposition of the blood cells when one cubic millimeter (1 mm$^3$) of sample blood is diluted with a physiological salt solution to 2000 parts per volume in the case of an erythrocyte count, and to 20 parts per volume in the case of a leucocyte count, and the space 27 is filled with this diluted sample blood. Formalin may be added to the diluted blood in order to render the blood cells immobile.

In the optical system illustrated in FIG. 3, a pair of converging lenses 29 converged the light beams 28 emitted from the source 17 in such a manner as indicated at 18 and 18'. The mirror 30 at the position 19 in FIG. 1 reflects upwards the thus converged beams, which then pass through the slit 31 and the condenser lens 32 thereby being adjusted in their intensity and made parallel with each other as indicated at 33. The light beams will then irradiate blood cells 34 contained within the sample plate 21 to thereby form an optical image 35. Subsequently, the image is magnified with five power magnification by means of the objective lens 36 and thereafter projected on the CCD assembly 37.

FIG. 4 is now referred to for an explanation of the one-way driving mechanism 38 which drives the sample holder 14. The sample plart 21 is slidably set at a predetermined position of the holder, and is inserted in an arrow direction (a), against a resilient force of a spring 39, thereby one end 14T of the holder operates a microswitch 40. One end of the spring 39 is fixed to a fixing member of a rail 41 which supports slidably the holder thereon, and in which a light-conducting hole 41H is provided. To an end of an arm 14A of the holder 14 to which the other end of the spring 39 is fixed, one end of a chain 42 is also fixed. The other end 42T of the chain 42 is fixed to one end of a spring 46 which is further fixed to a fixing point 2 of the apparatus. The chain 42 is stretched by means of a sprocket wheel 45S of a one-way clutch 45 which is set on a rotation shaft 44 of a motor 43 (for example, a synchronous motor with reduction gear), and thus chain 42 is always stretched by means of the spring 46. The one-way clutch 45, as shown in FIG. 5, comprises a ratchet wheel 48 and balls 49, such an arrangement enables the rotation of the sprocket 45S relative to the shaft 44, due to disengagement of the connection between the ratchet wheel 48 and the balls 49, only for the rotation in c-direction which corresponds to the movement of the holder 14 in a-direction, whereby, even when the motor 43 is not opened, the holder 14 can be set at the position as shown in FIG. 4. The microswitch 40 operates the motor 43, which ensures the engagement between the ratchet wheel 48 and the balls 49, due to the rotation of the shaft 44 in d-direction, whereby during the rotation of the sprocket 45S in the same direction the holder 14 is driven at a constant rate in the Y-direction, by means of the the urging force of the spring 39 attached to the arm 14A of the holder 14 as the chain 42 stretched around the sprocket 45S is driven thereby against the urging force of the spring 46.

When the sample plate 21 which is held on the holder 14 is passed above the light-conductive hole 41H, a projection 50 provided on the arm 14A operates a microswitch 51, whereby the motor 43 is stopped.

In such a manner as above described, the operation of both the microswitches 40 and 51 is actuated along a single axis of the excursion of the holder 14, and thus their operating position can be correct independently of any inherent dead-zone of operation of the micro switches themselves.

The circuit of the motor 43 comprises a self-holding circuit with relays, thus, for example, even when the holder 14 begins to scan in Y-direction, the circuit of the motor 43 remains ON.

By such an arrangement, when the holder 14 is scanned in the a-direction, the spring 39 is strongly strained by its own resilient force, and simultaneously the motor 43 begins to rotate with a constant rate of predetermined synchronous speed (fc) in d-direction, whereby the rotation of the sprocket 45S can be controlled, by means of the chain 42, in an appropriate scanning rate corresponding to the synchronous speed.

Supposing that the synchronous motor 43 has a rated torque (Ts) of 4 kg-cm under a continuous loading, a maximum braking torque will be nearly equal to twice the rated torque (Ts), i.e. 8 kg-cm which in turn correspond to a "pull out" or "step out" torque (Tw) of the motor. The power acting on the holder, namely the power of the spring 39 can be increased to a value near the maximum 2.7 kg-cm. This is one of the important features of the invention. Contrarily to this, in the event that the tractive force (F) for driving the sample holder should rely solely on the synchronous motor 43, its rated torque must be about 8 kg-cm which is twice as strong as the rated torque necessary in cases of jointly using a spring. In other words, it becomes possible in the invention to utilize a smaller motor having a rated torque (Ts) of 4 kg-cm, that is, half of 8 kg-cm.

It is also to be noted that the spring 39 is effective to remarkably improve the precision in the particle counts measurement. The spring is always urging the sample holder to closely follow the rotational motion of the motor in the scanning direction so that any play or looseness in the linkage members between said motor and said holder is taken up advantageously. This enables a correct detection of the minutest particles having diameter of a few microns.

In a case where the microswitch 51 fails to deenergize the motor driving circuit and the holder jams upon abutting something, the one-way clutch 45 permits the motor 43 to freely rotate thereby preventing seizure or scorching of the motor's coils.

When the sample holder 14 has advanced in the arrowed Y direction, the microswitch 51 is turned off thereby stopping the holder 14. At this moment, the indicator lamp 16 is switched off. One cycle of the scanning of said holder will finish in this manner in the direction shown with (Y).

FIG. 2A is referred to here again. A scanned area 58 is indicated with a dashed line in a central portion of the sample plate 21. The area is scanned to conduct a blood count test in accordance with the motion of said sample holder in the Y-direction. A width and a length of said area 58 are respectively for instance 1.28 mm and 10 mm. A line 59 is a start line of said motion. Said area 58 is enlarged in FIG. 6 wherein fine dots 60 on the upper and lower end portions represent red corpuscles. It should be understood apparent that said corpuscles entirely spread over the area though they are not shown in the middle portion of said area.

Two rigid lines at the start line 59 in FIG. 6 represent the CCD as shown in FIG. 3, the width ($l_3$) thereof in the Y-direction being 15 $\mu$m as referred to hereinabove. Therefore, a width of 3 $\mu$m in the X-direction of the scanned area 58 will be sensed by the CCD when the magnification of the aforedescribed optical system is 5 (five). The CCD 37 comprises 256 photoelectrical convertor elements that are spaced apart from each other and arranged in a row. The row has a length of 6.4 mm that corresponds to five times the width, i.e. 1.2 mm ($=l_1$), of the scanned 58 in the X-direction. In a case where the sample plate 21 moves at a speed of 2.2 mm/sec in the Y-direction, the CCD 37 will electronically scan the area 58 at small intervals (G) of 1 $\mu$m with an effective scanning width of 3 $\mu$m.

Figure 7:
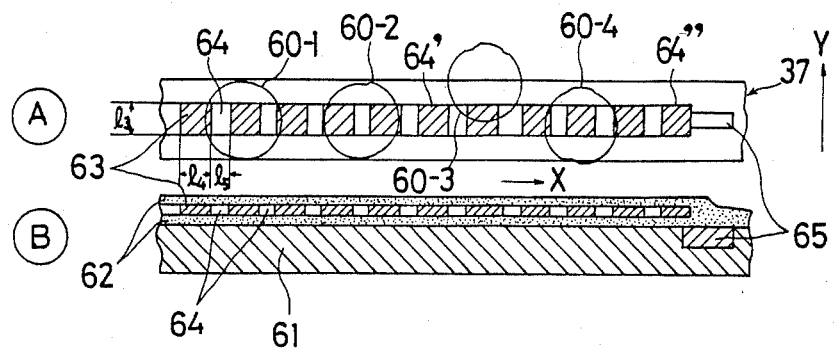
FIGS. 7A and 7B are respectively an enlarged plan view and an elevation of photoelectric convertor elements each being an integrated circuit such as CCD.

FIGS. 7A and 7B illustrate a principle of the blood count measurement based on the CCD. The numerals 60-1 to 60-4 indicate projected images of erythrocytes which are to be counted by the CCD 37, the magnification being 5 (five). An example of the CCD structure is illustrated in FIGS. 7A and 7B. A base plate 61 of a p-type semiconductor is covered with a thin layer 62 made of $SiO_2$. Small pieces 63 are made of for instance silicon (Si) as metallic electrodes at intervals of a small distance 64 wherein said pieces are arranged to form a row. Hatched portions in FIG. 7A do not represent any section but indicate silicon electrodes which respectively correspond to the photoelectric elements. The length ($l_3$) of said elements in the Y-direction is 15 $\mu$m, the width ($l_4$) thereof in the X-direction also being 15 $\mu$m. The width ($l_5$) of the distance 64 is 10 $\mu$m.

The elements 64' and 64'' are not covered with any erythrocyte image so that the light beams irradiate them without suffering any hindrance to thereby give rise to signal charges of 3 V on the portions of p-type semiconductor base plate 61 beneath said elements or electrodes 64', 64''. The element entirely covered with the image 60-1 will merely produce a low signal charge of 1 V because of the weakened light irradiating it.

These signal charges in each element are transferred in the X-direction one by one so as to be brought out from an n-type output gate 65. Such instantaneous transfer of electric charges is a self-scanning function peculiar to the CCD, i.e. a kind of integrated circuit, and will require for instance only about 0.002 sec. Particle counts are executed in such a manner as to compare each signal charge with a threshold value of 2 V that is a median of the abovesaid maximum and minimum signals, i.e. 3 V and 1 V. For example, one of the projected images 60-3 of a blood cell is covering about 60% of an element in the CCD so that a signal charge will approximately be 1.8 V. Consequently, since this charge is less than the threshold value (2 V) it will not be counted in this scanning line but sensed to be positive in the next scanning line. The latter line is spaced from the former line by the distance (G) of 1 $\mu$m in the Y-direction as shown in FIG. 6 so that the image 60-3 will entirely cover an element which is disposed in the next scanning line at a position corresponding to that of the element partially covered with the image 60-3 in FIG. 7A. On the other hand, each of the blood cell images 60-1, 60-2 and 60-4 is covering entirely one element, and therefore will be counted by each of the elements, respectively. All the erythrocytes existing within the scanned area 58 shown in FIG. 6 are counted in the above manner in a short time, e.g. 5 sec. The thus measured count is then corrected by means of a ratio of the volume of the diluted sample contained within the scanned area 58 to the volume of the diluted sample contained within the space 27 between the two protrusions of the sample plate 21 and then multiplying this value by the dilution coefficient. Such correction will give an accurate number of erythrocytes contained in 1 cubic mm ($mm^3$) of the undiluted sample; to be indicated on the digital counter 5 shown in FIG. 1. Thus, where for example as described above, a blood sample of 1 $mm^3$ is diluted to 2000 parts per volume and the containing volume of the scanned area 58 is ($l_1$)×($l_2$)×(thickness of space 27, i.e., 0.1 mm), then the correction factor applied to the measured count for obtaining an accurate blood count of the blood sample would be expressed as:

$$\frac{1 \text{ mm}^3}{(l_1 \times l_2 \times 0.1) \text{ mm}^3} \times 2000.$$

When a leucocyte count is to be performed, the erythrocytes are first broken with a proper reagent, and then the operations are conducted in the same manner as described hereinbefore.

Figure 8:
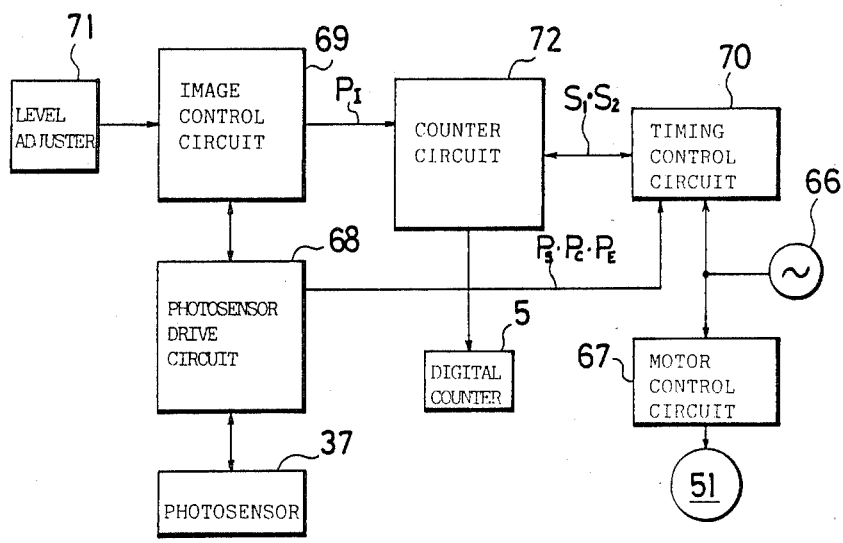
FIG. 8 is a block diagram of an electric circuit incorporated in the apparatus.

FIG. 8 illustrates an electric circuit acting as the counter means and controlling the above apparatus wherein the numeral 66 indicates an AC power source of 100 V which drives by means of a motor control circuit 67 the aforementioned synchronous motor 51 for the scanning mechanism. A photosensor drive circuit 68 receives output signals from the CCD, i.e. a photosensor 37, and feeds them to an image control circuit 69. The photosensor drive circuit 68 feeds also a pulse start signal (Pc), a clock pulse (Pc) and an end signal (PE) to a timing control circuit 70, the end signal being produced at each end of the scanning lines or detections in the X-direction. A clock pulse generator (not shown) may be provided within the drive circuit 68 or elsewhere.

The image control circuit 69 compares said signals fed from the drive circuit 68 with the aforementioned threshold value (i.e. 2 V) which is predetermined by a level adjustor 71. A differential amplifier contained in said control circuit 69 may be utilized to execute said comparison and to simultaneously amplify resulting differences. Subsequently, the control circuit 69 supplies to a counter circuit 72 a series of pulsed signal (Pi) each corresponding to corpuscles to be counted in the abovesaid manner.

On the other hand, the timing control circuit 70 produces a directive signal ($S_1$) and another directive signal ($S_2$) to charge them into the counter circuit 72, the former signal ($S_1$) thereby instructing said circuit 72 to count in the X-direction while the latter signal ($S_2$) instructing it to count in the Y-direction. Thus, the counter circuit 72 sums up counts for each scanning line and indicates a number of corpuscles on the digital counter 5 on said panel 4.

The present invention is not limited to the above embodiment but may be modified under various conditions. For example, the driving mechanism may employ a rack and pinion device in FIGS. 4 and 5 when an absolutely constant scanning velocity is desired. The tension spring may also be replaced with a compression spring. The microswitches can be replaced with other functional equivalents. The one-way clutch can be disposed on the motor shaft.

It will be appreciated that the invented apparatus is neither affected by any external noise nor will it suffer any clogging of sensor holes so that it is more advantageous than the known systems such as the impedance or photoelectric driving system. Its optical system and driving mechanism are more simply constructed than those of the large-sized apparatus currently used in big hospitals. Its low-torque small motor in the scanning mechanism is sufficient to assure a smooth scanning as well as a rapid return of the sample holder, thereby the small motor never becoming so over loaded as to burn. The invented apparatus is excellent not only in respect of easy operation but also in view of rapid and accurate corpuscle count. These advantages result from the ingenious utilization of the high sensitivity of the CCD. When the apparatus is used for clinical tests such as blood count, this can be performed and finished in a very short time, for instance 5 sec, without fear of blood cells coagulation.

What is claimed is:

1. An apparatus for counting numbers of fine particles, comprising:
    transparent sample plate means for containing a sample of fine particles to be counted, said sample plate means having a shape adapted to arrange said fine particles all on the same level across said plate without superposition;
    an optical system adapted to irradiate parallel light beams along an optical axis through said sample plate means for producing optical silhouetted images of said fine particles contained thereon and for magnifying and projecting said silhouetted images, and having self scanning charge coupled device (CCD) photoelectric converter means including a plurality of photoelectric elements arranged operably in a linear row array, said projected silhouetted images of said fine particles being magnified such that a projected image of a single fine particle has a dimension in the range of from one to five microns so as to substantially cover a single said photoelectric element, said photoelectric converter means being adapted to convert said magnified silhouetted images of said fine particles projected onto said photoelectric elements thereof into signal charges, said signal charges being transferred serially along the direction of said linear row array;
    drive means adapted to cause scanning motion of said sample plate means in a plane perpendicular to said optical axis of said optical system and in a direction perpendicular to said direction of said linear row array, and at a speed permitting scanning by said photoelectric converter means in said direction of said linear row array of said silhouetted images projected thereon as said sample plate means is moved, said drive means including sample holder means for holding said sample plate means, synchronous motor means operably coupled to said sample holder means for driving said sample holder means and spring means urging said sample holder means toward a direction in which said motor means drives said sample holder means, the urging force of said spring means on said sample holder being equal or greater than a rated driving torque of said motor means to a degree necessary for maintaining synchronous rotation of said motor means; and
    counting and output means for counting the numbers of said signal charges transferred serially along the direction of said linear row array of said photoelectric converter means which have a charge value greater than a predetermined charge threshold value and for summing said numbers of said charge signals exceeding said threshold value during said scanning motion of said sample plate means, and for outputting an output data signal representative of said summed number of said charge signals exceeding said threshold value.

2. An apparatus according to claim 1, wherein said drive means further comprises a reduction gear coupled to said motor means whereby the driving torque of said motor means is balanced with said urging force of said spring means acting on said sample holder means.

3. An apparatus according to claim 1 or 2 wherein driving torque of said motor means is converted into a linear force, said linear force being jointly applied to act on said sample holder means along with said urging force of said spring means.

* * * * *